(12) United States Patent
Nilsson et al.

(10) Patent No.: US 9,306,981 B2
(45) Date of Patent: Apr. 5, 2016

(54) BIOINFORMATIC PROCESSING SYSTEMS AND METHODS

(71) Applicant: Intertrust Technologies Corporation, Sunnyvale, CA (US)

(72) Inventors: Jarl Nilsson, Mountain View, CA (US); William Knox Carey, Mountain View, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 0 days.

(21) Appl. No.: 14/260,714

(22) Filed: Apr. 24, 2014

(65) Prior Publication Data

US 2014/0325587 A1    Oct. 30, 2014

Related U.S. Application Data

(60) Provisional application No. 61/815,702, filed on Apr. 24, 2013.

(51) Int. Cl.
| | |
|---|---|
| *H04L 29/06* | (2006.01) |
| *G06F 17/30* | (2006.01) |
| *G06F 21/62* | (2013.01) |
| *G06F 19/28* | (2011.01) |
| *G06F 17/00* | (2006.01) |
| *G06F 7/04* | (2006.01) |
| *G06F 7/00* | (2006.01) |
| *G06F 19/18* | (2011.01) |

(52) U.S. Cl.
CPC .......... *H04L 63/20* (2013.01); *G06F 17/30386* (2013.01); *G06F 17/30548* (2013.01); *G06F 19/28* (2013.01); *G06F 21/6227* (2013.01); *G06F 21/6245* (2013.01); *H04L 63/08* (2013.01); *G06F 19/18* (2013.01); *H04L 63/04* (2013.01); *H04L 63/10* (2013.01)

(58) Field of Classification Search
None
See application file for complete search history.

(56) References Cited

U.S. PATENT DOCUMENTS

| | | | |
|---|---|---|---|
| 5,892,900 A | 4/1999 | Ginter et al. | |
| 6,952,776 B1 * | 10/2005 | Chess | 713/188 |
| 7,430,585 B2 | 9/2008 | Sibert | |
| 8,234,387 B2 | 7/2012 | Bradley et al. | |
| 8,527,517 B1 * | 9/2013 | Ait-Mokhtar | 707/738 |
| 8,590,044 B2 * | 11/2013 | Trakic et al. | 726/24 |
| 2007/0180519 A1 | 8/2007 | Boccon-Gibod et al. | |
| 2012/0030220 A1 * | 2/2012 | Edwards et al. | 707/754 |

(Continued)

OTHER PUBLICATIONS

Callaway, E.; "Global Genomic Data-Sharing Effort Kicks Off"; Nature News; Mar. 6, 2014; pp. 1-2.

(Continued)

*Primary Examiner* — Shin-Hon Chen
(74) *Attorney, Agent, or Firm* — Finnegan, Henderson, Farabow, Garrett & Dunner, LLP

(57) ABSTRACT

The present disclosure relates to systems and methods for facilitating trusted handling of genomic and/or other bioinformatic information. Certain embodiments may facilitate policy-based governance of access to and/or use of bioinformatic information, improved interaction with and/or use of distributed bioinformatic information, parallelization of various processes involving bioinformatic information, and/or reduced user involvement in bioinformatic workflow processes, and/or the like. Further embodiments may provide for memoization processes that may persistently store final and/ or intermediate results of computations performed using genomic data for use in connection with future computations.

22 Claims, 14 Drawing Sheets

(56) References Cited

U.S. PATENT DOCUMENTS

2012/0260346 A1 10/2012 Carey et al.
2013/0096943 A1 4/2013 Carey et al.
2013/0269031 A1* 10/2013 Nakao et al. .................... 726/22

OTHER PUBLICATIONS

Gymrek, M. et al.: "Identifying Personal Genomes by Surname Inference"; Science, vol. 339, No. 6117; Jan. 18, 2013; pp. 321-324.
Homer, N. et al.; "Resolving individuals contributing trace amounts of DNA to highly complex mixtures using high-density SNP genotyping microarrays"; PLoS Genetics; vol. 4,. No. 8; Aug. 2008; pp. 1-9.
Kolata, G.; "Poking Holes in Genetic Privacy"; New York Times, Jun. 16, 2013; pp. 1-3.
Lemke, A.A. et al.; "Public and Biobank Participant Attitudes toward Genetic Research Participation and Data Sharing"; Public Health Genomics; vol. 13; Jan. 15, 2010; pp. 368-377.
Lunshof, J. et al.; "From Genetic Privacy to Open Consent"; Nature Reviews | Genetics; vol. 9; May 2008; pp. 406-411.
Nyholt, D. et al.; "On Jim Watson's *APOE* status: genetic information is hard to hide"; European Journal of Human Genetics; vol. 17, No. 2; Feb. 2009; pp. 147-149.
Sankararaman, S. et al.; "Genomic privacy and limits of individual detection in a pool"; Nature Genetics; vol. 41, No. 9; Sep. 2009; pp. 965-967.

* cited by examiner

```
// Topology
phenoselect -> genoselect;
genoselect :> genomatch;
genomatch -> count;

// Template parameters
type phenoselect {
    template: odbc
    endpoint: "driver=mysql;database=phenodb;server=localhost;UID=root;PWD=*trophe"
    expression: "SELECT id FROM employee WHERE cancer=1"
} type genoselect {
    template: lookup
```

```
o    {started,  'node1@127.0.0.1',<0.88.0>,    phenoselect}
o    {started,  'node1@127.0.0.1',<0.92.0>,    genoselect}
o    {started,  'node2@127.0.0.1',<6443.69.0>,genoselect}
o    {started,  'node3@127.0.0.1',<6696.81.0>,genoselect}
o    {started,  'node4@127.0.0.1',<6697.81.0>,genoselect}
o    {started,  'node1@127.0.0.1',<0.94.0>,    genoselect}
o    {started,  'node2@127.0.0.1',<6443.71.0>,genoselect}
o    {started,  'node3@127.0.0.1',<6696.83.0>,genoselect}
o    {started,  'node4@127.0.0.1',<6697.83.0>,genoselect}
o    {finished,'node1@127.0.0.1',<0.88.0>,    phenoselect}
o    {started,  'node1@127.0.0.1',<0.96.0>,    genoselect}
o    {finished,'node1@127.0.0.1',<0.94.0>,    genoselect}
o    {result,  false}
o    {started,  'node1@127.0.0.1',<0.98.0>,    genomatch}
o    {finished,'node1@127.0.0.1',<0.98.0>,    genomatch}
o    {finished,'node2@127.0.0.1',<6443.69.0>,genoselect}
o    {started,  'node2@127.0.0.1',<6443.73.0>,genomatch}
o    {result,  false}
o    {finished,'node2@127.0.0.1',<6443.73.0>,genomatch}
o    {finished,'node2@127.0.0.1',<6443.71.0>,genoselect}
o    {result,  false}
o    {started,  'node2@127.0.0.1',<6443.74.0>,genomatch}
o    {result,  true}
o    {finished,'node2@127.0.0.1',<6443.74.0>,genomatch}
o    {finished,'node3@127.0.0.1',<6696.81.0>,genoselect}
O    ...
```

Figure 4

```
500 type credentials {
    user: bob
    authtoken: PIpZiITSDMh2yfd5Q3wsMs99x8g=
    expires: 2013-04-01T00:00:00Z
} type genoselect like credentials {
```

Figure 5

```
600 phenoselect => ABCInstitute: genoselect;

type genoselect like credentials {
    template: gene-server
    endpoint: "https://10.0.1.17"
    location: (15, 72635778, 72668520)
}
```

Figure 6

BIOINFORMATIC PROCESSING SYSTEMS AND METHODS

RELATED APPLICATIONS

This application claims the benefit of priority under 35 U.S.C. §119(e) to U.S. Provisional Patent Application No. 61/815,702, filed Apr. 24, 2013, and entitled "BIOINFORMATIC PROCESSING SYSTEMS AND METHODS", which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY

The present disclosure relates generally to systems and methods for facilitating trusted handling of genomic and/or other bioinformatic information. More specifically, but not exclusively, the present disclosure relates to systems and methods for enabling secure, governed, and/or audited use of genomic and/or bioinformatic information.

Genetic testing is moving from detection of Single Nucleotide Polymorphisms ("SNPs")—isolated individual chemical differences in genetic code—to Whole Genomic Sequencing ("WGS"), which records every base pair in a genetic sequence. Genomic sequencing information may be used in connection with a variety of applications including, for example, molecular and evolutionary biology studies. For example, in molecular biology studies, genomic information may be used in connection with identifying new genes, identifying potential drug targets, identifying genetic associations with certain diseases and/or conditions, and/or the like.

Bioinformatics workflows, including workflows involving genomic information, may involve a series of manually assembled and/or performed serial/sequential steps. For example, in a connection with a bioinformatic workflow process, a researcher may download gigabytes of genomic data included in unaligned data files from a public and/or private repository (e.g., using file transfer protocol ("FTP") or the like). The unaligned data may, for example, be processed by a vendor-provided tool and/or a special purpose program or script.

Aligned output files may be processed and/or analyzed by a "variant caller" (e.g., a Java language variant caller) to identify locations of genetically interesting features in each of the aligned output files. A set of subjects (e.g., a cohort) from a database or other collection of medical information may be selected. Aligned output files associated with each subject in the cohort may be processed and/or analyzed to identify particular mutations or other features of interest. Output information from this processing/analysis may be collected and statistically analyzed in connection with the researcher's studies.

The above-described exemplary workflow may introduce several potential problems, including, for example:

Lack of Data Governance—

The above-described workflow may assume that researchers have the right to access genomic data of interest (e.g., data included in unaligned data files from a public and/or private repository). In some instances, however, individuals, organizations, and/or governmental authorities may place certain restrictions on the access and/or use of genomic data. For example, certain jurisdictions may have laws governing the distribution of genomic data to outside the jurisdiction.

Similarly, the above-described workflow may lack auditing and/or management capabilities governing access to and/or use of genomic data. For example, after the initial download of genomic data, a researcher's activities in connection with the use and/or distribution of the data may not be readily ascertained and/or tracked. In view of these limitations, the above-described exemplary workflow may not be well-suited for use in connection with genomic data that has certain associated access and/or use restrictions.

Centralized Information—

The above-described workflow involves downloading genomic data to a centralized location for processing and analysis (e.g., downloaded from one or more public and/or private repositories). Such a data centralization process may require significant resources, and may not be particularly practical when genomic data is distributed across multiple databases. Moreover, as discussed above, certain genomic data may be associated with a jurisdiction that does not allow distribution of the data from the jurisdiction. Accordingly, centralized gathering of genomic data that includes data from a restrictive jurisdiction may need to be performed within that jurisdiction.

Sequential Workflow—

As discussed above, the various constituent steps of the exemplary workflow may be performed sequentially and/or serially by a centralized computing system. Such sequential and/or serial processing and/or analysis may require significant computing resources by the centralized system performing the activities.

User Involvement—

Many constituent processes in the above-described workflow involve direct user interaction. For example, a user may be involved in selecting genomic data to download to a centralized processing location. Direct user involvement in connection with the workflow may consume time and/or other resources of a researcher that could otherwise be spent on more productive activities.

Systems and methods are described herein that ameliorate some or all of these potential problems. For example, in certain embodiments, the disclosed systems and methods can be used to enable secure and/or policy-based access to and/or use of bioinformatic information including, without limitation, genomic information. Among other things, the disclosed systems and methods may facilitate policy-based governance of access to and/or use of bioinformatic information (e.g., distribution, analysis, etc.), improved interaction with and/or use of distributed bioinformatic information, parallelization of various processes involving bioinformatic information, reduced user involvement in bioinformatic workflow processes, and/or the like.

In certain embodiments, the disclosed systems and methods may use structured workflow specifications and/or syntaxes for defining certain processes involving bioinformatic information. Such specifications and/or syntaxes may facilitate a variety of activities including, for example, genomic data and/or cohort selection, target variant selection in connection with research and/or other activities utilizing bioinformatic information, parallelization of various bioinformatic processing and/or analysis functions, protection of certain personal information relating to individuals associated with bioinformatic information (e.g., personally identifiable information ("PII")), and/or the like. In some embodiments, the disclosed specification and/or syntax structure may enable a user to specify and/or implement various bioinformatic information workflows and/or processes in connection with one or more associated computer systems.

In further embodiments, the disclosed systems and methods may enable persistent storage of results of computations and/or analyses performed using various bioinformatic information. In certain embodiments, final and/or intermediate results of computations performed using bioinformatic information may be persistently stored for use in connection with future computations using a memoization process. In certain embodiments, utilizing prior and/or intermediate computational results in connection with new computations may provide certain processing efficiencies and/or improvements in computational speeds.

BRIEF DESCRIPTION OF THE DRAWINGS

The inventive body of work will be readily understood by referring to the following detailed description in conjunction with the accompanying drawings, in which:

FIG. 3 illustrates an exemplary workflow specification consistent with embodiments of the present disclosure.

FIG. 4 illustrates an exemplary result of instantiating and running a specification consistent with embodiments of the present disclosure.

FIG. 5 illustrates an example of sharing authentication credentials across multiple modules consistent with embodiments of the present disclosure.

FIG. 6 illustrates an exemplary syntax for specifying a domain consistent with embodiments of the present disclosure.

DETAILED DESCRIPTION

Figure 1:
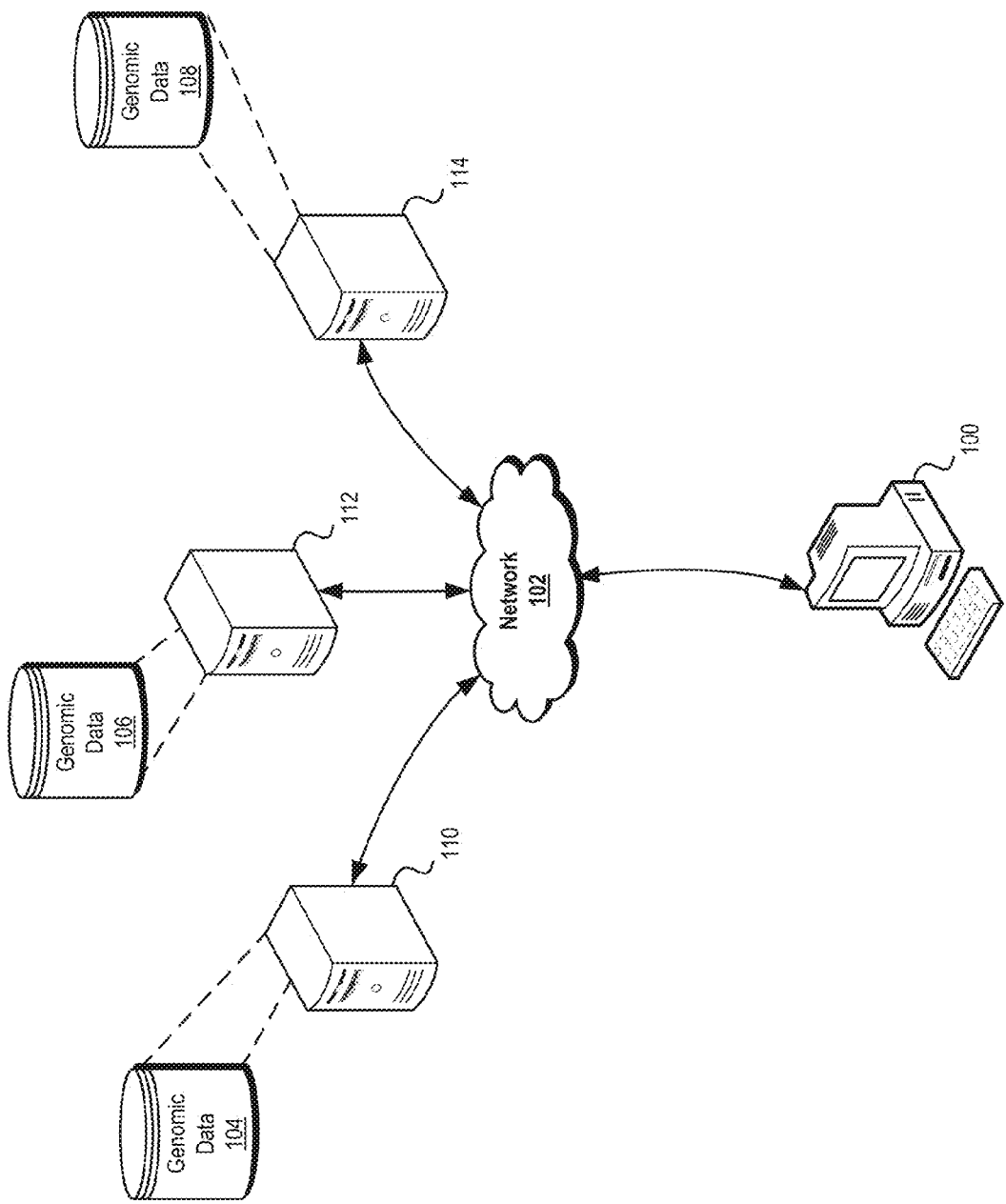
FIG. 1 illustrates an exemplary ecosystem for storage, management, and processing of genomic data consistent with embodiments of the present disclosure.

A detailed description of systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented that facilitate secure, governed, and/or audited use of genomic and/or bioinformatic information. In certain embodiments, the disclosed systems and methods can be used to enable policy-based governance of access to and/or use of genomic data, improve interaction with and/or use of distributed genomic data, facilitate parallelization of processes involving genomic data, reduce user involvement in genomic data workflow processes, and/or the like. In some embodiments, the disclosed systems and methods may use structured workflow specifications and/or syntaxes for defining certain processes involving genomic data. In further embodiments, the disclosed systems and methods may provide for memoization processes that enable certain results of computations based on genomic data to be retained and used in connection with future computations. It will be appreciated that these systems and methods are novel, as are many of the components, systems, and methods employed therein.

In certain embodiments, the systems and methods described herein can, for example, be used in connection with digital rights management ("DRM") technologies such as those described in commonly assigned U.S. patent application Ser. No. 11/583,693, entitled "Digital Rights Management Engine Systems and Methods," and filed Oct. 18, 2006 ("the '693 application"), service orchestration and DRM technologies such as those described in commonly assigned U.S. Pat. No. 8,234,387, entitled "Interoperable Systems and Methods for Peer-to-Peer Service Orchestration", and filed Jun. 7, 2004 ("the '387 patent"), information governance technologies such as those described in commonly assigned U.S. patent application Ser. No. 13/444,624, entitled "Information Security Systems and Methods", filed Apr. 11, 2012

("the '624 application"), and/or information processing technologies such as those described in commonly assigned U.S. patent application Ser. No. 13/654,349, entitled "Systems and Methods for Protecting and Governing Genomic and Other Information", filed Oct. 17, 2012 ("the '349 application") (the contents of '693 application, the '387 patent, the '624 application, and the '349 application hereby being incorporated by reference in their entireties), as well as in other contexts.

Genomic Data Processing Ecosystem

FIG. 1 illustrates an exemplary ecosystem for storage, management, and processing of genomic data 104-108 consistent with embodiments of the present disclosure. As used herein, the terms "genomic data" and/or "genomic information" may generally refer to data expressing, representing, and/or derived from the entirety or a portion of a genome or genome sequence. This data may include, without limitation, information encoded in chemical structures such as DNA, mRNA, and proteins as well as related regulatory information such as methylation status. As used herein the term "genome" may refer to an organism's hereditary information. A genome may be encoded in DNA or RNA, and may be represented as mRNA or as protein sequences derived from these nucleic acid sequences. The term "genome" may include both genes and non-coding sequences. When applied to a specific organism, the term "genome" can refer to genomic data from normal cells—including mitochondrial DNA—and also genomic data from related cells such as tumors and other organisms of the microbiome. Although embodiments of the disclosed systems and methods are discussed herein in connection with genomic data, it will be appreciated that the disclosed systems and methods may also be used in connection with any other suitable information, including, for example, any other type of bioinformatic information.

A client system 100 may provide a variety of functions allowing a user to process, analyze, and/or otherwise interact with genomic data 104-108. In certain embodiments, the client system 100 may be communicatively coupled with one or more genomic data storage and/or processing systems 110-114 via one or more networks 102. The one or more genomic data storage and/or processing systems 110-114 may, among other things, be configured to store and/or manage genomic data 104-108 and/or interact with the client system 100 in connection with the same. In certain embodiments, the client system 100 may be associated with a service and/or an application or process that may access and/or otherwise remotely use information stored by the one or more genomic data storage and/or processing systems 110-114 to perform various operations thereon. For example, an application executing on the client system 100 may enable a user of the system to interact with one or more genomic data storage and/or processing systems 110-114 in connection with performing various workflow processes and/or analyses using the genomic data 104-108 consistent with embodiments disclosed herein.

The one or more networks 102 may comprise a variety of network communication devices and/or channels and may use any suitable communication protocols and/or standards facilitating communication between the client system 100, the genomic data storage and/or processing systems 110-114, and/or one or more other systems. Network 102 may comprise the Internet, a local area network, a virtual private network, and/or any other communication network utilizing one or more electronic communication technologies and/or standards (e.g., Ethernet or the like). In some embodiments, the network 102 may comprise a wireless carrier system, such as a personal communications system ("PCS"), and/or any other suitable communication system incorporating any suitable communication standards and/or protocols. In further embodiments, the network 102 may comprise an analog mobile communications network and/or a digital mobile communications network utilizing, for example, code division multiple access ("CDMA"), Global System for Mobile Communications or Groupe Speciale Mobile ("GSM"), frequency division multiple access ("FDMA"), and/or time divisional multiple access ("TDMA") standards. In certain embodiments, the network 102 may incorporate one or more satellite communication links. In yet further embodiments, the network 102 may use IEEE's 802.11 standards, Bluetooth®, ultra-wide band ("UWB"), Zigbee®, and/or any other suitable communications technology or technologies.

The client system 100 and/or the genomic data storage and/or processing systems 110-114 may comprise a variety of computing devices and/or systems, including any computing system or systems suitable to implement the systems and methods disclosed herein. Systems 100, 110-114 may, for example, comprise a variety of computing devices and systems, including without limitation laptop computer systems, desktop computer systems, sever computer systems, distributed computer systems, smartphones, tablets, and/or the like. It will be appreciated that any suitable configuration of computing systems and storage media could be used in connection with the connected systems 100, 110-114, including without limitation, a single server or cluster of servers, or a distributed collection of heterogeneous computer systems connected by a variety of networks (e.g., such as the Internet, public and/or private networks, and/or the like).

In certain embodiments, the client system 100 and/or the genomic data storage and/or processing systems 110-114 may comprise at least one processor system configured to execute instructions stored on an associated non-transitory computer-readable storage medium. As discussed in more detail below, the client system 100 and/or the genomic data storage and/or processing systems 110-114 may further comprise a secure processing unit ("SPU") configured to perform aspects of sensitive operations such as trusted credential and/or key management, secure policy management, and/or other aspects of the systems and methods disclosed herein. The client system 100 and/or the genomic data storage and/or processing systems 110-114 may further comprise software and/or hardware configured to enable electronic communication of information between the devices and/or systems 100, 110-114 via the network 102 using any suitable communication technology and/or standard.

The genomic data storage and/or processing systems 110-114 may be configured to store, manage, process, distribute, and/or update certain genomic data 104-108 stored thereon. In certain embodiments, the genomic data storage and/or processing systems 110-114 may be associated with one or more processing domains, jurisdictions, organizations, institutions, users, locations and/or the like. As an example, genomic data storage and/or processing system 110 and associated genomic data 104 may, for example, be associated with a research institution, genomic data storage and/or processing system 112 and associated genomic data 106 may, for example, be associated with a jurisdiction that does not allow distribution of genomic data 106 from the jurisdiction, and genomic data storage and/or processing system 114 and associated genomic data 108 may, for example, be associated with a business organization offering genomic data 108 as a data product for research purposes. In certain embodiments, the genomic data storage and/or processing systems 110-114 may be associated with one or more cloud-based systems for the trusted storage and analysis of genetic and/or other information, and may incorporate embodiments of the systems and methods disclosed in connection with the '349 application.

As discussed above, an application executing on the client system 100 may enable a user of the system to interact with the one or more genomic data storage and/or processing systems 110-114 in connection with performing various workflow processes and/or analyses using the genomic data 104-108. In certain embodiments, the client system 100 may be configured to issue certain requests/queries to the genomic data storage and/or processing systems 110-114 directing the genomic data storage and/or processing systems 110-114 to perform certain processes and/or operations using genomic data 104-108 stored thereon. Results of the processes and/or operations may be returned to the client system 100 from the associated genomic data storage and/or processing systems 110-114. In certain embodiments, such results may obfuscate, anonymize, and/or otherwise filter PII and/or other phenotypical data associated with the genomic data 104-108, such that a user of the client system 100 may not ascertain and/or readily ascertain PII from results derived from the genomic data 104-108.

In some embodiments, the one or more genomic data storage and/or processing systems 110-114 may include varying levels of hardware and/or software security hardening based on the security of the genomic data 104-108 stored thereon. For example, genomic data 104-108 that does not include information associating particular genetic sequences with identification information regarding associated individuals (e.g., names, addresses, Social Security numbers, etc.) may be protected by a less security-hardened system than genomic data 104-108 that includes such associations.

In certain embodiments, prior to interacting with genomic data 104-108 managed by the one or more genomic data storage and/or processing systems 110-114, the client system 100 and/or a user thereof may authenticate their identity and/or rights to access and/or otherwise use the genomic data 104-108. For example, username and/or password authentication, biometric authentication, personal identification number authentication, and/or any other suitable type of user authentication may be used in connection with authentication of the rights of the client system 100 and/or a user thereof to access and/or use the genomic data 104-108.

The one or more genomic data storage and/or processing systems 110-114 and/or the client system 100 may be configured to enforce privacy and/or policies associated with the genomic data 104-108 specified by stakeholders in the data (e.g., associated individuals, institutions that gathered the data, governmental authorities responsible for enforcing certain jurisdictional restrictions on the access or distribution of the data, etc.). The policies may articulate certain restrictions, conditions, requirements, and/or other actions associated with the access, use, distribution, and/or the like of the genomic data 104-108. Such policies may be enforced in connection with access, use, distribution, and/or the like of the genomic data 104-108 by the client system 100 and/or a user thereof. For example, a policy may articulate that only users authenticating their possession of certain access credentials may use certain genomic data 104-108 managed by the one or more genomic data storage and/or processing systems 110-114 and/or derive certain computational results therefrom. Policies may articulate, without limitation, policies preventing and/or otherwise restricting the access, use, and/or distribution of genomic data 104-108, policies articulating that certain security requirements be met prior to access, use, and/or distribution of genomic data 104-108, policies articulating that certain actions be performed in connection with the access, use, and/or distribution of genomic data 104-108, and/or the like. A variety of other types of policies may be associated with genomic data 104-108, and any type of policy articulating any restrictions, conditions, requirements, and/or actions to be enforced in connection with the access, use, and/or distribution of the genomic data 104-108 may be used in connection with the disclosed embodiments. In some embodiments, such policies are expressed and enforced using digital rights management technologies such as those described in the '693 application and/or the '387 patent, previously incorporated by reference herein, although it will be appreciated that any suitable policy expression and enforcement technologies could be used.

It will be appreciated that a number of variations can be made to the architecture and relationships presented in connection with FIG. 1 within the scope of the inventive body of work. For example, without limitation, in some embodiments, some or all of the functions performed by the client system 100 may be performed by the one or more genomic data storage and/or processing systems 110-114. Similarly, some or all of the functions performed by the one or more genomic data storage and/or processing systems 110-114 may be performed by the client system 100. Thus it will be appreciated that FIG. 1 is provided for purposes of illustration and explanation, and not limitation.

Genomic Information Workflow Overview

Figure 2:
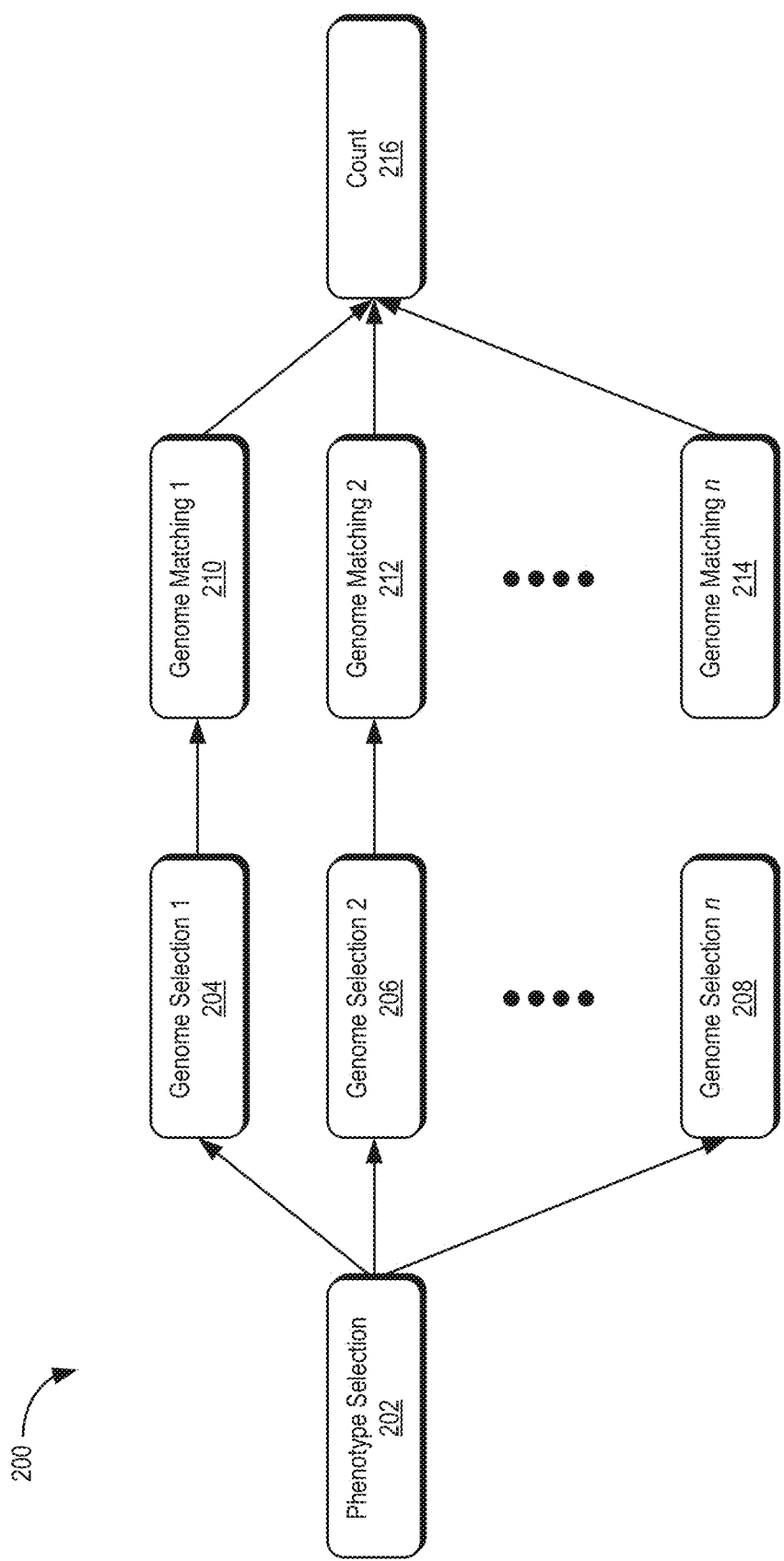
FIG. 2 illustrates an exemplary workflow process for interacting with genomic data consistent with embodiments of the present disclosure.

FIG. 2 illustrates an exemplary workflow process 200 for interacting with genomic data consistent with embodiments of the present disclosure. For example, the illustrated workflow process 200 may be used in connection with identifying a prevalence of a particular variant within a population. In certain embodiments, a workflow process involving genomic data may, at a high level, be specified by a query having a particular syntax. For example, the syntax may express a group of individuals to which a user is permitted access and/or use of associated genomic data, a particular trait and/or condition associated with a population of interest, and a targeted variant of interest.

As an example, an example specification of a workflow process may be expressed according to the following:

U|pancreatic cancer|% KRAS variant 4

In the above example, the specification may be interpreted as the being associated with the following workflow process: (1) start with a universe of U individuals to which a user has permission to access associated genomic data (e.g., as articulated by enforced policy or the like), (2) filter the universe of U individuals by selecting individuals with a record of pancreatic cancer and (3) compute a percentage of those individuals that exhibit a particular genetic variant (e.g., a KRAS variant 4).

The above specification may hide certain details regarding an underlying workflow process. For example, the specified universe of individuals, U, may represent a set of all genomic data and/or records to which a particular user has access (e.g., as determined by enforced policy or the like), a specified subset of such data, and/or the like. This set may depend on the user, articulated policy associated with the corresponding genomic data and/or records, and/or the like. In certain embodiments, the set may change dynamically based on an overall context of a specified workflow process. For example, due to policy restrictions, the size of the set may increase or decrease depending on a type of operation to be performed on associated genomic data articulated by the query specification.

The second step, filtering the universe of U individuals by selecting a cohort of individuals with a record of pancreatic cancer, may hide certain details regarding where associated phenotypical data is located, what types of databases are being used to store the data, and/or the like. The third step, computing a percentage of the cohort with a particular genetic variant, may hide even further detail. For example, the location and storage format of the associated genomic data, which may be distributed across a plurality of servers, organizations, laboratories, and/or jurisdictions, is not specified by the specification. Furthermore, the specification may not specify that, in certain instances, genomic data may be analyzed and/or processed in parallel.

In certain embodiments, the above-described exemplary query specification may implement the workflow process 200 illustrated in FIG. 2 to identify a prevalence of a particular variant within a population. In certain embodiments, the various constituent operations included in the illustrated workflow process 200 may be performed by one or more functional modules 202-216 (e.g., software modules and/or the like) configured to execute on a client system, one or more genomic data storage and/or processing systems, and/or any other suitable system or combination thereof.

As shown, a phenotype selection module 202 may select a cohort from a phenotypical database (e.g., a database containing medical records and/or other phenotypical information or the like). For example, the phenotype selection module 202 may select a cohort having a particular trait (e.g., pancreatic cancer) from a set of individuals that a user of a client system has rights to access associated genomic data.

In certain embodiments, genomic data associated with a selected cohort may be distributed across multiple genomic data storage and/or processing systems (e.g., systems in different jurisdictions, associated with different institutions, and/or the like). For example, genomic data associated with a selected cohort may be distributed across different jurisdictions or different institutions, and may not be readily centralized due to various legal restrictions associated with the jurisdictions or institutions, and/or logistics of a data centralization process (e.g., cost, limited centralized storage capacity, etc.). Accordingly, in certain embodiments, various operations associated with certain functional modules 204-214 in the workflow process 200 may be performed by multiple genomic data storage and/or processing systems (e.g., performed in parallel).

In certain embodiments, for each subject in the selected cohort, associated genomic data may be selected, retrieved, extracted and/or otherwise identified by genomic data selection modules 204-208. In certain embodiments, a selection module of the genomic data selection modules 204-208 may extract genomic data stored and/or managed by associated genomic data storage and/or processing system executing the selection module or in communication therewith. For example, genomic data selection module 204 may select, retrieve, extract, and/or otherwise identify genomic data associated with a subject of a cohort stored by a first genomic data storage and/or processing system, genomic data selection module 206 may select, retrieve, extract, and/or otherwise identify genomic data associated with a subject of a cohort stored by a second genomic data storage and/or processing system, and/or the like. In this manner, genomic data selection modules 204-208 may operate on various distributed genomic data stored and/or managed by a plurality of associated genomic data storage and/or processing systems (e.g., operating and/or processing in parallel or the like).

Genomic data selected, retrieved, extracted and/or otherwise identified by genomic data selection modules 204-208 may be processed by genomic data matching modules 210-214 to identify the presence and/or absence of a particular variant and/or characteristic in the genomic data using any suitable genomic data analyzing technique. The results of the processing by the genomic data matching modules 210-214 (e.g., whether processed genomic data for a subject in a selected cohort includes and/or does not include a particular variant and/or characteristic of interest) may be passed to one or more other modules for further processing. For example, in FIG. 2 the results are passed to a counting module 216 that may compute a percentage and/or number of subjects in the selected cohort having genomic data that includes and/or does not include the variant and/or characteristic of interest.

Workflow Instantiation

In certain embodiments, to instantiate the exemplary workflow process described above and illustrated in connection with FIG. 2, a user may specify and/or implement a variety of subroutines and/or sub-processes. In certain embodiments, the subroutines and/or sub-processes may not substantially change when certain modifications to a query specification are changed and, accordingly, may be used in connection with a variety of specified workflow processes. In some embodiments, workflow instantiation may include, without limitation, some or all of the following activities:

A user may specify a query to be performed in connection with a phenotypical database (e.g., a medical record database or the like). In certain embodiments, the query may be specified as an SQL statement. In other embodiments, the query may be specified in another structured format and/or in a more unstructured format (e.g., a natural language specifications, etc.), and thus it will be appreciated that any suitable format could be used based, e.g., on what query language or format a particular database (or databases) supports. In some embodiments, the query may be distributed across a plurality of databases, and a user may collate results returned in response to the query from the databases at a client system.

A database query may include credentials that identify a requesting user. Such credentials may be used in connection with authenticating a user's identity and/or associated rights to access and/or otherwise use genomic data.

Access to a database including phenotypical and/or genomic data and/or use of such data may be audited by a genomic data storage and/or processing system and/or other database management system and/or by a system that processes an access request (e.g., a client system and/or the like). In certain embodiments, such auditing may provide a variety of information relating to the access to and/or use of phenotypical and/or genomic data.

A user may implement logic that takes predefined data sets (e.g., each row, in some embodiments) returned in response to a database query and forward this data as an individual parameter to a genotyping stage (e.g., genomic data selection and/or matching processes).

A user may implement distribution logic that takes a defined data set (e.g., a row) returned in response to a database query and forwards it as an individual parameter to a genotyping stage (e.g., genomic data selection and/or matching processes). In certain embodiments, such distribution logic may be sensitive to resources available to a particular user and/or the user's ability and/or rights to command resources on remote systems.

A user may identify individual systems to which genotyping requests (e.g., requests for genomic data selection and/or matching processes) are made and may send genotyping process requests to the identified systems.

A user may implement methods to ensure that systems having access to genomic data are provisioned with certain versions of software required to properly interrogate the genomic data.

A user may map phenotypical identification information associated with individual subjects that are returned in response to a database query to corresponding genomic identification information associated with the subjects' genomic data.

A user may generate and/or initiate a system to generate one or more database queries based on the genomic identification information. A user may further generate and/or initiate one or more systems to collect various results from the database queries, process the results (e.g., compute associated statistics, identify particular characteristics and/or variants, etc.), and return the results of the processing to a user.

For various processes including in a workflow, a user may create adapter routines that ensure that the processes can communicate results to subsequent processing stages in a manner that modules implementing subsequent processing stages may understand.

Some or all of the above activities may be streamlined by embodiments of the disclosed systems and methods, thereby improving the ability of a user to specify and implement a desired workflow. In certain embodiments, a user may implement a workflow by generating a workflow specification. FIG. 3 illustrates an exemplary workflow specification 300 consistent with embodiments of the present disclosure.

The illustrated workflow specification 300, which may, for example, be embodied as a software file having a .spc extension, may describe a desired workflow. In certain embodiments, the workflow specification 300 may specify a way to instantiate functional modules used in connection with a workflow from one or more templates and connect those instances together. The workflow specification 300 may include, among other things, a description of a problem and/or workflow process topology and/or a set of parameters from individual computational modules used in connection with the workflow process.

For example, in the illustrated workflow specification 300, under the comment line "// Topology", a topology of a workflow process consistent with the process illustrated in connection with FIG. 2 is specified. The topology is specified as including a module named "phenoselect" that will send its output (in parallel) to one or more instances of a module named "genoselect." In the illustrated specification 300, the equal-arrow syntax, "=>", may specify that the module provided on the right side of the syntax is a module having multiple instances. The topology further includes a specification that each instance of the "genoselect" module may send its output to a "genomatch" module on a 1:1 basis. In certain embodiments, the colon-arrow syntax, ":>", may be used to specify this aspect of the process topology. Finally, the exemplary topology specifies that each "genomatch" module may send results to an instance of a "count module". In certain embodiments, the collection of multiple outputs into a single node and/or module may be represented in the specification 300 by a single-arrow syntax "→".

Under the comment line "// Template parameters", each of the functional modules named in the topology may be parameterized. In certain embodiments, the topology and template specifications may be presented in any order in connection with the workflow specification 300 (e.g., interspersed in the file). The specified parameters may include one or more named key-value pairs that may determine how software code for a particular module will be instantiated and/or parameterized.

In some embodiments, a "template" keyword may be used to identify a template file, which may be embodied as a software file having a .tpl extension. A template file may include template code for creating an instance of an associated module. In some embodiments, the template may operate by keyword substitution. In some embodiments, a keyword for which a value is specified in the specification 300 using a substitution syntax may be substituted into a corresponding location in a template file. For example, for a key-value pair "name: Bob" in the specification 300, a template file may specify a command "print "Hello $(name)"". When this template is instantiated, the value "Bob" may be substituted for "$(name)", resulting in the code "print 'Hello Bob'".

In some embodiments, to instantiate a workflow process from a specification 300 and various template files, a system may compile the specification 300 into executable or interpretable code that may be executed or interpreted on a suitable system. In certain embodiments, a system that may manage instances of parallel execution, security, auditing, and/or database access processes may be used, such as the system described in the '349 application.

FIG. 4 illustrates an exemplary result 400 of instantiating and running a specification consistent with embodiments of the present disclosure. For example, the exemplary result 400 may be generated by instantiating the specification described above in connection with FIG. 3. As shown in FIG. 4, the specification may be executed asynchronously and/or in parallel. The "node#@ 127.0.0.1" notation may refer to different computational nodes in the system, each of which may manage one or more processes. In the example parameterization generating the illustrated result 400, ten matches from the "phenomatch" module were found and distributed across four nodes for computation. In certain embodiments, the computational nodes may be associated with a single system. In further embodiments, the computational nodes may be associated with a plurality of distributed systems and/or locations (e.g., different data centers and/or the like). In some embodiments, the system may automatically manage distributing processes that perform computations across the various nodes and/or handle communication between various nodes.

A variety of other syntax elements may be included in a workflow specification file that may, among other things, allow for creation of more advanced workflows. For example, a "like" syntax may allow one type to extend another, thereby incorporating associated key-value pairs. This syntax allows, for example, authentication credentials to be shared across multiple modules. FIG. 5 illustrates an example 500 of sharing authentication credentials across multiple modules consistent with embodiments of the present disclosure.

In the illustrated example 500, when the "genoselect" module is instantiated, the keys "user", "authtoken", and "expires" may be substituted as if they had been specified in the "genoselect" module directly. In some embodiments, this mechanism may allow common variables to be shared across multiple modules. In certain embodiments, a type may "like" any number of other types.

In a specification file, various functional modules may be restricted to run in one or more specified domains (e.g., groupings of computing and/or storage resources). In certain embodiments, the aforementioned functional modules may be parallelized across a default domain. In other embodiments, a writer of a specification file may dictate that certain computations be assigned to differing sets of resources. In certain embodiments, this functionality may be useful in connection with directing a computation to occur in a domain that has access to a specific resource that the computation requires.

As an example, an institution (e.g., the ABC Institute) in the United Kingdom may store genomic data associated with a particular individual, John Smith. The institution may have a data access policy that prohibits distribution of raw genomic data associated with John Smith. Using a domain specification in a specification file, a user may direct an operation on John Smith's genome to be performed within the institutions' domain (e.g., on a system associated with the institution or the like). FIG. 6 illustrates an exemplary syntax 600 for specifying a domain consistent with embodiments of the present disclosure.

In the illustrated exemplary syntax 600, the "phenoselect" module is specified as being parallelized over a set of resources specified by the domain "ABCInstitute". When a domain is mentioned in a specification file, a system may attempt to load a second file named after the domain (e.g., a file having a .dom extension or the like). Accordingly, in the example syntax 600, the mention of "ABC Institute" may cause the system to load "ABCInstitute.dom" to specify a set of resources that comprise the domain.

Figure 7:
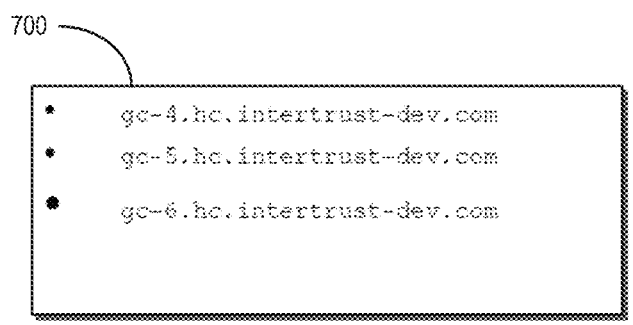
FIG. 7 illustrates an example of specification of a domain consistent with embodiments of the present disclosure.

FIG. 7 illustrates an example 700 of specification of a domain consistent with embodiments of the present disclosure. The illustrated example 700 includes a list of endpoints to which computations and/or associated modules may be assigned. In further embodiments, the list may contain other domain parameters such as access credentials and/or the like. In certain embodiments, the specification of domain parameters may also be included in connection with a list of endpoints to which computations may be assigned.

In certain instances, a designated domain of a computation may be a function of a previous computation. In some embodiments, a plus-arrow syntax, "+>", may be used to specify that messages passing between two nodes should be inspected and routed to an appropriate domain. For example, if a specification file includes a line indicating "x+>y", the instance "x" may be assumed to produce tagged outputs of the format "{domain, Msg}", where "domain" is the computation domain to which messages should be routed, and ""Msg" is the message to send to that domain."

In another example of use of a plus-arrow syntax operator, a distributed hash table style lookup module may take desired genomic identification information associated with an individual and return a location for associated genomic data (e.g., a location expressed in terms of a computation domain). For example, in such an embodiment, an output for the associated individual, whose genomic data may be stored by the ABC Institute in the United Kingdom, may be a tuple of the domain and the genomic identification information (e.g., "{ABCInstitute, 0123456789abcdef}"). The tuple may automatically be routed to the "ABCInstitute" domain. Another tuple (e.g., "{ebi, c0dec0dec0dec0de}"), may be routed to the "ebi" domain.

Genetic Variant Carrier Identification

Figure 8:
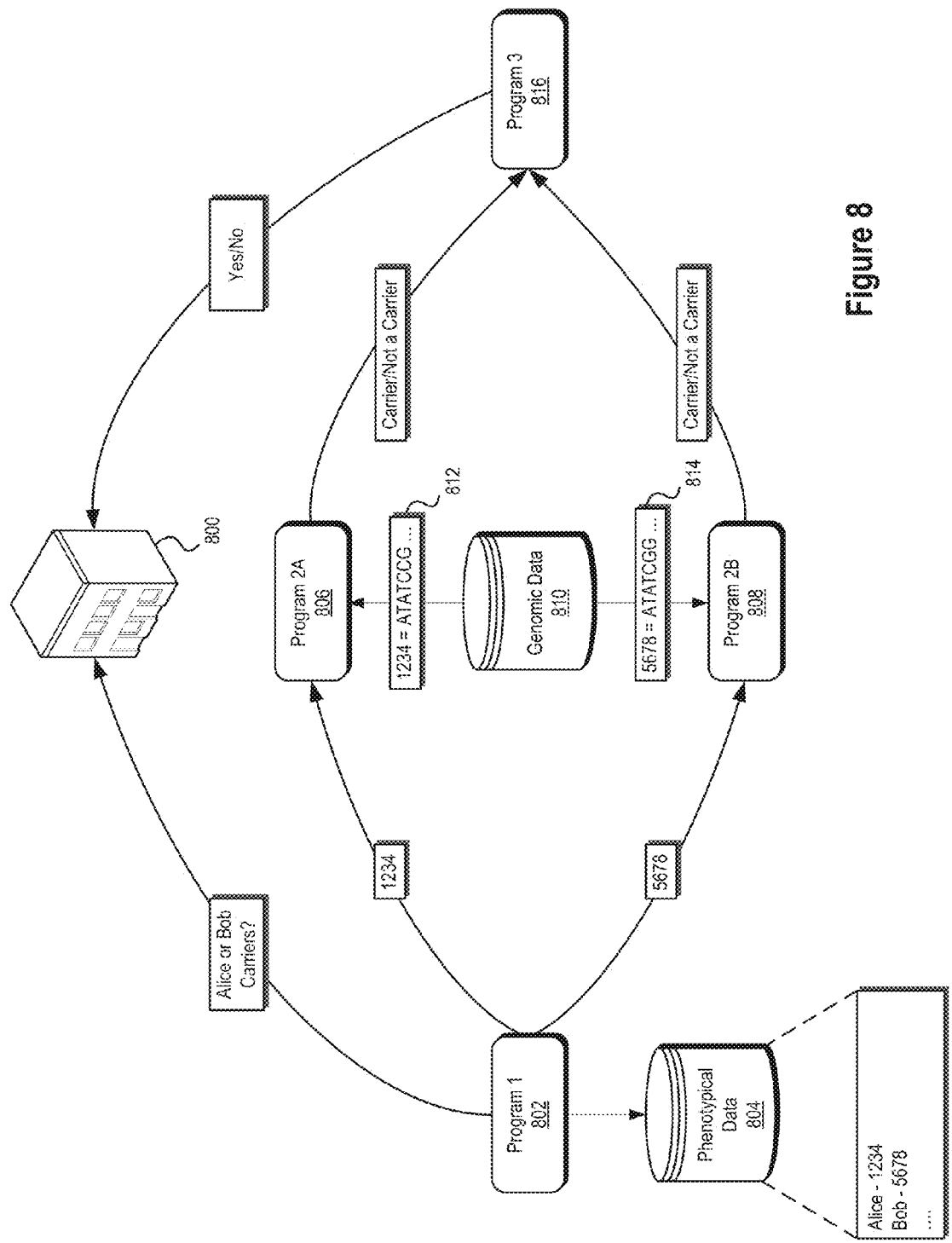
FIG. 8 illustrates an exemplary workflow process for identifying certain variants in genomic data consistent with embodiments of the present disclosure.

FIG. 8 illustrates an exemplary workflow process for identifying certain variants in genomic data consistent with embodiments of the present disclosure. Particularly, in connection with the illustrated workflow, a genetic counseling service 800 may offer a genetic testing service designed to determine whether two individuals are both carriers of a particular genetic variant. For example, in certain embodiments, such a service 800 may provide an indication of a probability that the offspring of the two individuals will be born with a specific genetic disorder, such as Tay-Sachs Disease. Consistent with embodiments disclosed herein, a carrier screening process may receive genomic data associated with both individuals, determine whether the individuals are a carrier for the disease, and/or determine a likelihood that the individuals' offspring will be born with the disease of interest. For purposes of this illustrative example, if both parents are carriers of a particular genetic variant, their offspring have a 25% chance of having a disease and a 50% chance of being a carrier, and if neither of the individuals are carriers, their offspring have no chance of having the disease or being a carrier.

In the above simplified example, the screening process may reveal to the genetic counseling service 800 the carrier status of both patients with 100% certainty. In certain instances, however, the individuals may not wish to have this personal information made known to third parties with such certainty. Accordingly, in some embodiments, the process may be implemented in a manner such that personal information, such as individual carrier status, may not be revealed and/or may otherwise be obfuscated to the genetic counseling service 800 while still allowing the counseling service 800 to identify situations where individuals are more likely to have offspring with a particular disease.

In certain embodiments, certain aspects of a carrier screening workflow process may operate on genomic data associated with individuals in a manner that is not visible to the service 800. For example, as illustrated, the counseling service 800 may issue a request to a first program 802 implementing a first part of the screening process. The request may identify the names (or other identification information) of two individuals, Alice and Bob, that the service 800 wishes to analyze to determine whether their offspring have a risk of developing a particular disease.

The first program 802 may access phenotypical data 804 associating the identification information provided with the request with anonymized genomic data identification information and identify genomic data identification information associated with the requested individuals. For example, as illustrated, the phenotypical data 804 may associate the names included in the request (e.g., Alice and Bob), with randomized identifiers (e.g., 1234 and 5678) associated with their corresponding genomic data. In certain embodiments, the first program 802 may be associated with a first processing domain (e.g., a first computer system and/or the like) that does not store and/or otherwise have direct access to genomic data associated with the genomic data identification information. Accordingly, if the security of the first processing domain is compromised, an attacker may not access genomic data associated with an individual based solely on knowledge of the phenotypical identification information associated with the user (e.g., a name or the like). In some embodiments, the first program 802 may not provide the genomic data identification information to the genetic counseling service 800, thereby preserving the anonymity of the genomic data identification information.

After identifying genomic data identification information associated with the requested individuals, the first program 802 may send the genomic data identification information to one or more second programs 806, 808. For example, as illustrated, genomic data identification information associated with Alice, 1234, may be sent to second program 806, and genomic data identification information associated with Bob, 5678, may be sent to second program 808.

Based on the genomic data identification information, the second programs 806, 808, may retrieve corresponding genomic data 812, 814 from a genomic database 810. The second programs 806, 808 may have access to one or more genomic databases 810 associating genomic data identification information of an individual with genomic data of the individual. For example, second program 806 may use genomic data identification information associated with Alice to retrieve genomic data associated with Alice 812 from the genomic database 810. Similarly, second program 808 may use genomic data identification associated with Bob to retrieve genomic data associated with Bob 814 from the genomic database 810.

The second programs 806, 808, may be configured to analyze the retrieved genomic data 812, 814 to determine whether the genomic data 812, 814 exhibits a particular variant indicative of carrier status. The second programs 806, 808 may send the results of this determination to a third program 816. In certain embodiments, the results may not include identification information associated with individuals. For example, the results may indicate a binary carrier status (e.g., "Carrier" or "Not a Carrier") without including any information regarding an individual associated with the carrier status. In this manner, the results may not be used to associate a carrier status with a particular individual.

The third program 816 may indicate, based on the carrier results generated by the second programs 806, 808, whether the results indicate that both individuals are carriers, and thus at an elevated risk of having offspring with a disease of interest. The third program 816 may send this result to the genetic counseling service 800. In some embodiments, this result may be a binary result indicating whether both individuals are carriers of a variant of interest (e.g., "Yes" or "No"). In this manner, in response to the initial request issued by the genetic counseling service 800 regarding whether both individuals are carriers, the counseling service 800 may receive a binary affirmative or negative response. Accordingly, individual carrier status is only reveled to the genetic counseling service 800 in the case that both individuals are carriers, which may be exceedingly rare. For example, the probability is approximately 0.14% even in the most at-risk population for Tay-Sachs Disease, and thus, in this example, the probability is small that private information associated with the individuals would be revealed by the illustrated process.

In certain embodiments, the first program 802, the second programs 806, 808, and/or the third program 816 may be executed in a single processing domain and/or execution environment and/or plurality of processing domains and/or execution environments. In certain embodiments, executing the first program 802, the second programs 806, 808, and the third program 816 in a plurality of different domains and/or execution environments may help to maintain the security of personal information and/or genomic data in the event one or more of the domains and/or execution environments is compromised. For example, if a processing domain of the third program is compromised, an attacker may access information regarding the carrier status of two unknown individuals, but may not access PII information associating the carrier status with the two particular individuals. In this manner, in some embodiments, the processing domains may provide for an execution environment that may execute programs that analyze genomic data without revealing an unacceptable amount of intermediate information to a creator of the data analyzing program or a service using the same (e.g., a genetic counseling service 800).

Memoization Overview

Figures 9, 10:
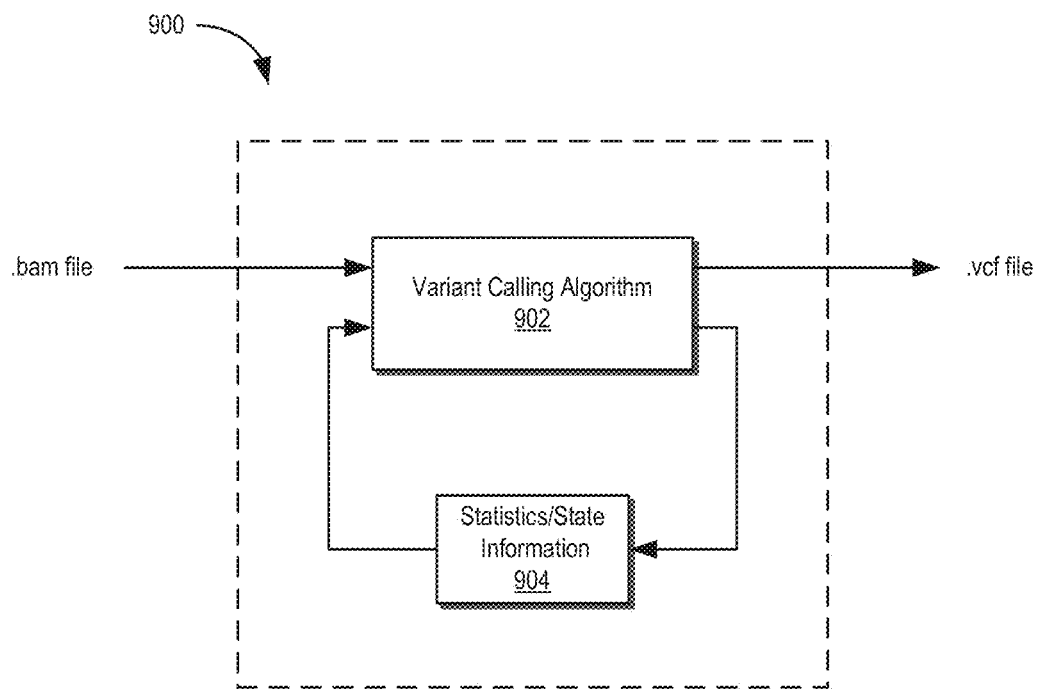
FIG. 9 illustrates a conceptual diagram of a variant identification program consistent with embodiments of the present disclosure.
FIG. 10 illustrates an exemplary workflow specification including a referentially transparent type specification consistent with embodiments of the present disclosure.

Many conventional bioinformatics routines may not be particularly optimized to run across large data sets and/or on parallelized hardware and/or software domains and/or execution environments. For example, variant identification programs, such as the GATK program available from the Broad Institute, may be used to identify features of interest in genomic data. FIG. 9 illustrates a conceptual diagram 900 of a variant identification program consistent with embodiments disclosed herein.

As illustrated, a variant identification program may be configured to receive one or more binary genome sequence files (e.g., .bam files). The variant identification program may produce a file (e.g., a .vcf file) containing identified variants for the genomic data included in the received binary genome sequence files. For example, a variant calling algorithm 902 of a variant identification program may be used to identify variants included in genome data associated with the received binary genome sequence files. As part of this process, the variant calling algorithm 902 may produce and/or use various statistics and/or state information 904 associated with the variant calling process.

In certain circumstances, the accuracy of the variant identification process may depend upon a number of genomes input into the variant identification program. For example, a larger number of genomes input may yield a more accurate set of variant calls and/or identifications (e.g., by building a body of relevant statistics and/or state information 904 associated with the variant calling process). In some embodiments, the variant identification process may be batch-oriented. Accordingly, achieving a high degree of variant identification accuracy on a single genome may involve providing a much larger reference set of genomes to the variant calling algorithm 902.

The larger reference set may be used internally by the program to compute various statistics and/or state information 904 that enables more accurate variant calling by the variant calling algorithm 902. Consistent with embodiments disclosed herein, a memoization process may be used to enable results of certain computations based on genomic data to be retained and used in connection with future computations. For example, through a memoization process, intermediate statistics and/or state information 904 may be stored persistently for reuse in connection with future runs of the variant calling algorithm 902, thereby saving a large amount of future re-computation and accelerating the variant identification process. In certain embodiments, the memoization process may separate variant analysis functions of a variant identification program from associated computation states. The variant analysis functions may include the algorithms for computing variant calls, and the computation states may maintain a state of the computations on persistent storage.

Some computation nodes or modules may be referentially transparent—that is, they may produce the same output deterministically in response to the same input. For example, to implement a memoization process, the computation unit may not use internal randomization or fetch parameters from other input devices, and all input parameters may be known before the computation is started. Based on this behavior, intermediate results may be cached in persistent storage and used in connection with future computations. In certain embodiments, to signal that a function is referentially transparent, a specification file may use an appropriate keyword (e.g., "memo" or the like) before a "type" specification, as illustrated in the specification file 1000 illustrated in FIG. 10.

In the illustrated specification 1000, correspondence between the inputs and outputs of the "genoselect" instance in the "ABCInstitute" domain may be persistently stored. As a result, a downstream function that depends on a particular computed value may receive the value relatively quickly because the computation may be avoided if its results have been previously cached. In some embodiments, the memoization process may depend on persistently storing a correspondence between inputs and outputs of an associated process. In certain embodiments, if the code for the function is opaque, the disclosed memoization process may treat the function as black box. In other embodiments, some or all partial computation results may be persistently stored for future use.

In certain embodiments, a result may be analyzed to determine if it should be stored in persistent storage or if it should be recalculated in connection with future computations. In some embodiments, this determination may depend on a variety of factors including, without limitation, an amount of available persistent storage, the cost of the storage, the cost of moving output data from the storage versus re-computation, and/or the like. In certain embodiments, memoization processes may be integrated in a manner that allows a user to use previously-computed results from another user if such reuse is allowed by associated access policies.

In certain embodiments, to avoid persistently storing all possible input values in connection with a memoization process and to facilitate faster lookup, the input values may be stored as cryptographic hashes, signatures, or other values, which may then be used to look up a previously computed output. In certain embodiments, cryptographic hashing may further be performed on instructions associated with a computation. In some embodiments, a table may be used to store persisted input and/or output combinations and/or hashes thereof for use in connection with future computations.

Figure 11:
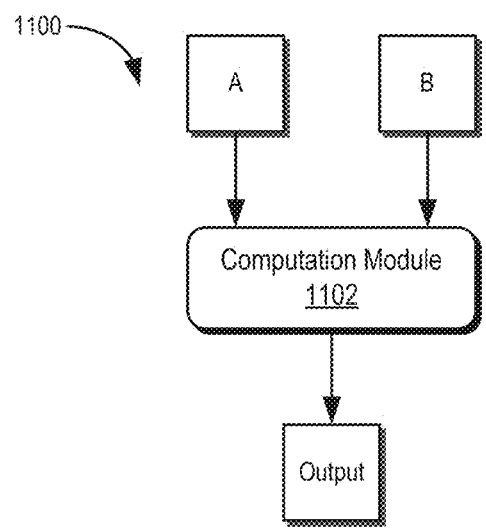
FIG. 11 illustrates a conceptual diagram of a computation having two inputs and one output consistent with embodiments of the present disclosure.

FIG. 11 illustrates a conceptual diagram 1100 of a computation having two inputs and one output consistent with embodiments of the present disclosure. As illustrated, a computation module 1102 may receive two inputs, "A" and "B", and produce an output. In certain embodiments, the computational module 1102 may produce a deterministic output—that is, the computational module 1102 may produce the same output deterministically in response to the same input.

Figure 12:
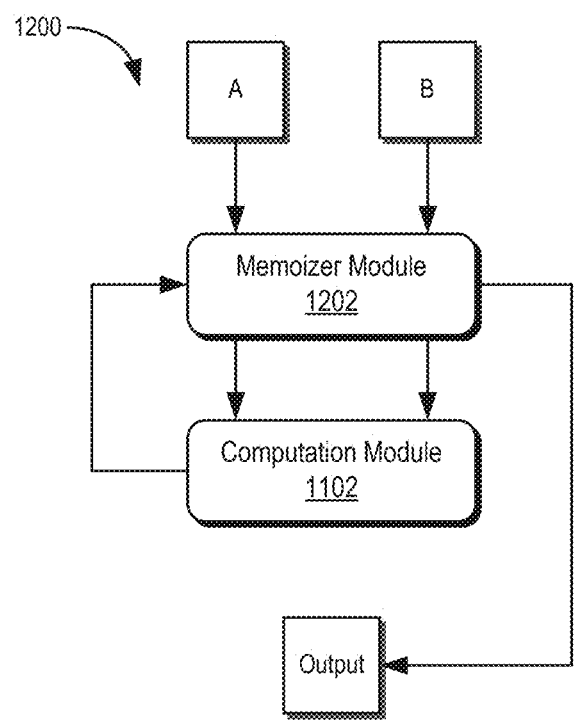
FIG. 12 illustrates a conceptual diagram of a computation including a memoization module consistent with embodiments of the present disclosure

FIG. 12 illustrates a conceptual diagram 1200 of a computation including a memoization module 1202 consistent with embodiments of the present disclosure. As illustrated, the computation has two inputs, "A" and "B", and one output. In one embodiment, to implement a memoization process, the inputs may be provided to a memoization module 1202. The inputs may further be provided by the memoization module 1202 to the computational module 1102 that may produce an output based on the same. The output may be provided to the memoization module 1202 for storage as well as being output from the computation. In this manner, the memoization module 1202 may persistently store the inputs and their associated outputs. In certain embodiments, computed hashes or some other identification of the received inputs and/or outputs (sometimes referred to herein as a signature of the computation) may be persistently stored by the memoization module 1202 to facilitate subsequent lookup and retrieval.

In connection with subsequent computations, the memoization module 1202 may generate a hash or other identifier based on the received inputs and/or instructions associated with the computation. The memoization module 1202 may compare this hash or other identifier to a table of known values and computation results. If no match is found, the computation may proceed by providing the received inputs to the computation module 1102 to compute an output as described above. If a match is found, the memoization module 1202 may provide the associated output as an output for the computation without having to re-compute the output based on the received inputs. It will be appreciated that while, for purposes of illustration, hash values are used in this and other examples as a look-up mechanism, any suitable look-up mechanism(s) could be used to identify and retrieve the results of previous computations. It will also be appreciated that the memoization process described herein could be implemented in any suitable manner, and that the examples shown in FIGS. 12-16 are provided for purposes of illustration, and not limitation. For example, in some embodiments, the process illustrated in FIG. 12 could be implemented by, e.g., simply inserting code into the program illustrated in FIG. 11 to check, prior to performing a computation, whether the computation has been previously performed (and the results stored), and, if so, retrieving and using (or returning) that result, and, if not, performing the computation and storing the result for future use.

Memoization and Multi-Node Computations

Figure 13:
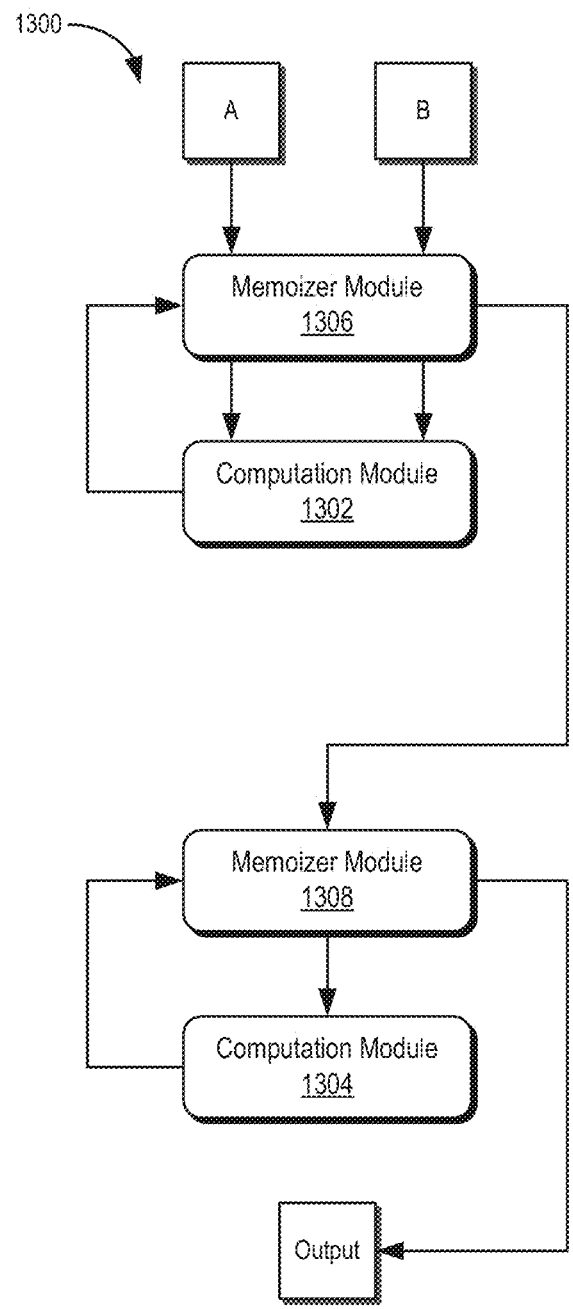
FIG. 13 illustrates a conceptual diagram of a computation including a plurality of constituent computations implementing memoization processes consistent with embodiments of the present disclosure

FIG. 13 illustrates a conceptual diagram 1300 of a computation including a plurality of constituent computations implementing memoization processes consistent with embodiments of the present disclosure. Particularly, the illustrated computation may receive two inputs, "A" and "B", to produce an output. In connection with the producing the output, the illustrated computation may use two computational modules 1302, 1304 configured to perform constituent steps of the computation. For example, a first computation module 1302 may be configured to produce an output based on the received inputs, "A" and "B", and provide this output to a second computational module 1304 as an input for use in connection with generating an output of the overall computation.

To implement a memoization process, the inputs, "A" and "B", may be provided to the first memoization module 1306 prior to being provided to and/or in additional to the first computational module 1302. The first computational module 1302 may produce an output based on the received inputs, and may provide the generated output to the first memoization module 1306. The first memoization module 1306 may persistently store the inputs and the output from the first computational module 1302 for use in connection with future computations. As discussed above, in some embodiments, hash values of the received inputs, instructions associated with the computation, and/or the output of the first computational module 1302 may be persistently stored by the first memoization module 1306.

The output from the first computational module 1302 may be provided (e.g., by the first memoization module 1306) as an input to the second memoization module 1308 prior to being provided to and/or in additional to the second computational module 1304. The second computational module 1304 may generate an output based on the input (and possibly other inputs, not shown) and provide the output to the second memoization module 1308. The second memoization module 1308 may persistently store the input and the output from the second computational module 1302 for use in connection with future computations. In some embodiments, hash values of the received inputs, instructions associated with the computation, and/or the deterministic output of the second computational module 1304 may be persistently stored by the second memoization module 1308.

The exemplary computation illustrated in FIG. 13 integrates memoization processes in connection with constituent computational steps of a multi-step computation. In further embodiments, in lieu of or in addition to integrating memoization in connection with constituent computational steps, an overall computational output of a multi-step computation may be used in connection with a memoization processes. For example, in certain instances, information stored as part of a memoization process involving constituent steps of a computation may not be likely to be used in connection with future computations. Accordingly, storing output from constituent steps using the disclosed memoization processes may not be necessary.

Figure 14:
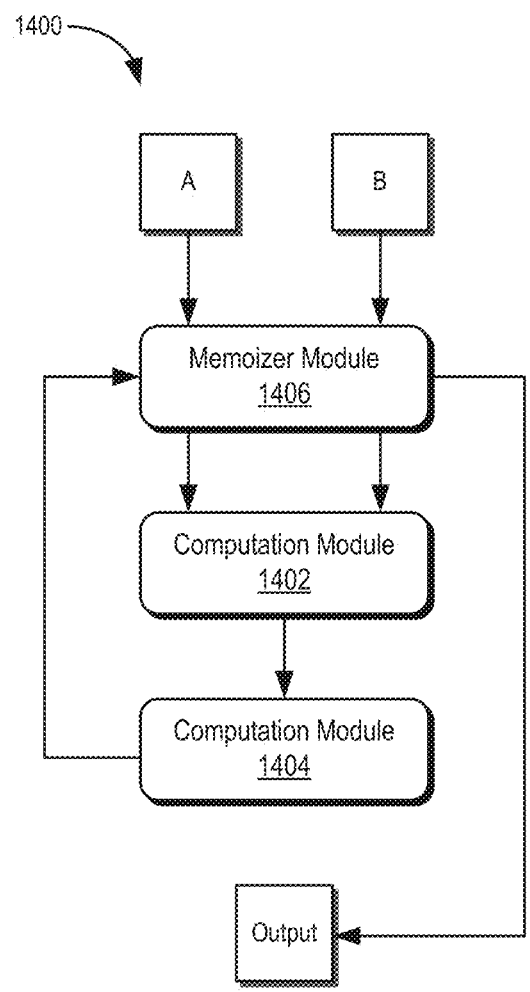
FIG. 14 illustrates another conceptual diagram of a computation including a plurality of constituent computations implementing memoization processes consistent with embodiments of the present disclosure.

FIG. 14 illustrates another conceptual diagram 1400 of a computation including a plurality of constituent computations implementing memoization processes consistent with embodiments of the present disclosure. As illustrated, the computation may use first and second computational modules 1402, 1404, to perform steps of a multi-step computational process. Consistent with embodiments disclosed herein, a single memoization module 1406 may be used to persistently store inputs, instructions associated with the computation, and/or generated outputs and/or information relating to the same (e.g., hashed values or the like) of the overall computational process. Such a memoization implementation may be used in computational situations where information relating to constituent process steps may not be of particular interest in connection with future computations.

Memoization in Bioinformatics Computations

In some embodiments, memoization techniques may be used in connection with various bioinformatics computations, including, for example, genomic data computations such as those described herein. In certain embodiments, all and/or part of information persistently stored as part of a memoization process may reside locally under the control of an associated memoization module and/or may be associated with a remote module and/or computing system that other systems executing computational processes may access.

Information persistently stored as part of a memoization process may be managed in any suitable manner. For example, cost/benefit calculations and/or heuristic algorithms can be used to determine the efficacy of storing certain information. For example, persistent storage of information that is commonly and/or recently used in connection with a computation may be prioritized over storage of information that is not commonly used and/or has not been recently used (e.g., prioritized in connection with efficient lookup operations, deletion activities in the event of limited storage space, and/or the like). In certain embodiments, persistently stored information may be managed in a manner such that looking-up relevant information in connection with future computations takes less time and/or is otherwise more efficient than performing the computation again.

In certain circumstances, genomic data may be relatively similar between individuals. For example, genetic similarity between two human individuals may be higher than 99.9%. Genetic similarity between humans and yeast may be approximately 50%. Given the inherent similarity in genomic data, certain computations performed in connection with genomic data may often be repeated in connection with later computations. For example, a computation performed on a portion of genomic data may likely have already been performed in connection with prior research investigations. Accordingly, memoization processes may be used to look-up outputs associated with the prior computations (e.g., genetic variant identification and/or disease risk computations, etc.), thereby saving computational time and/or resources in connection with requests for certain later computations. In some embodiments, a service (e.g., a web service) can be provided to facilitate the lookup and retrieval of the results of computations. Requests to the service can specify inputs, and a lookup can be performed to see if the service has access to a corresponding output. In some embodiments, the outputs could be stored in a central repository, while in other embodiments the results could be distributed amongst multiple repositories or other locations. In some embodiments, the service might return the result of the computation to the caller of the service, and in other embodiments, the service might simply redirect the caller to a location where the result could be obtained.

Policy-Driven Memoization Processes

In certain embodiments, memoization nodes and/or modules in a computational process may be policy-driven. For example, in certain jurisdictions, legal requirements may not allow genomic data within the jurisdiction to be accessed from outside the jurisdiction. Jurisdictional requirements may further stipulate that genomic data may only be operated on within the jurisdiction by some trusted authority.

To accommodate such jurisdictional requirements, a computational module may be located in a jurisdiction and/or domain different from the jurisdiction and/or domain of an associated memoization module. For example, if allowed by associated policy, a computational module may operate within a jurisdiction restricting the access of associated genomic data from outside the jurisdiction, while a memoization module associated with the computational module may operate outside the jurisdiction. In this manner, the computational module may comply with the jurisdiction's requirements, but results of associated computations persistently stored by the memoization module may be readily accessed outside the jurisdiction for use in connection with future computations.

In addition to persistently storing information regarding inputs to a computation, corresponding outputs, and/or hashes or other identifiers thereof, in some embodiments, other parameters may be persistently stored as part of a memoization process. For example, credential information and/or policy information provided as part of a policy-managed computation may be stored as inputs by a memoization module for use in connection with future computations. Like the computation inputs and/or outputs, in some embodiments, hashes of the credential information and/or policy information may be persistently stored to increase look-up efficiency and/or integrity verification in connection with future computations.

Figure 15:
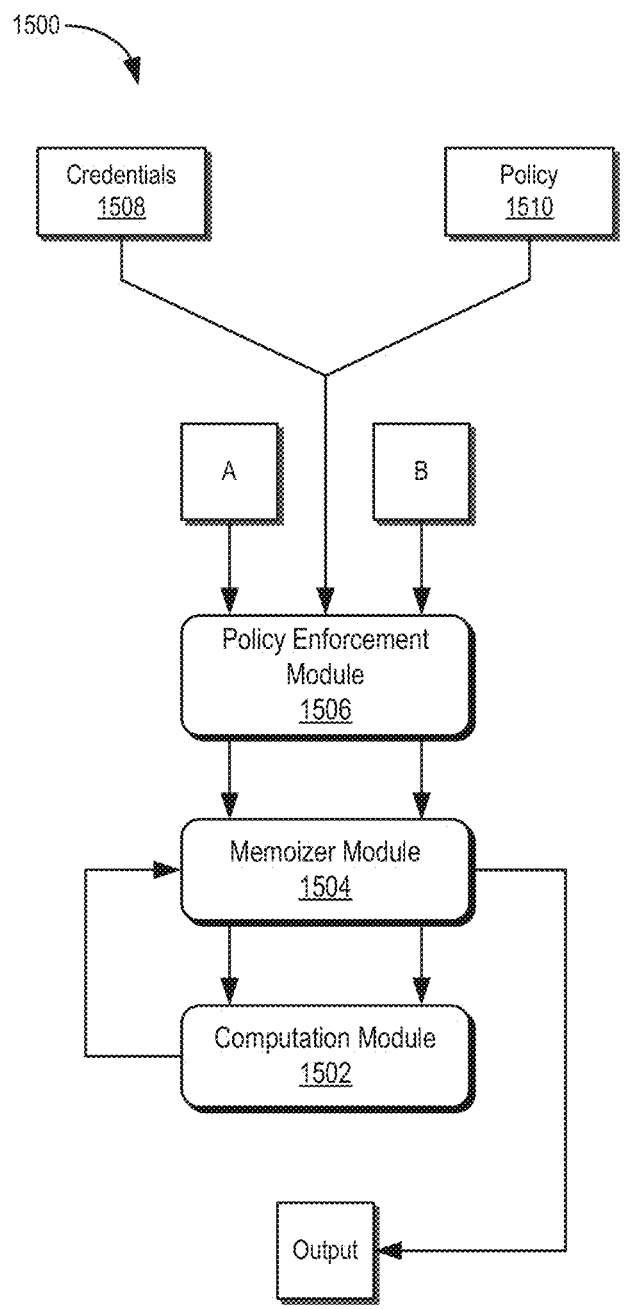
FIG. 15 illustrates a conceptual diagram of a computation implementing policy-driven memoization processes consistent with embodiments of the present disclosure.

FIG. 15 illustrates a conceptual diagram 1500 of a computation implementing policy-driven memoization processes consistent with embodiments of the present disclosure. As illustrated, various information may be provided to a policy enforcement module 1506 in connection with a computation including, without limitation, inputs (e.g., "A" and "B"), credentials 1508 (e.g., credentials of a user requesting the computation be performed), and/or policy information 1510 associated with the user, the computation, and/or the inputs. Based on the received inputs, the policy enforcement module 1506 may determine whether the requested computation is allowed by policy and can proceed.

If the computation is allowed to proceed, the inputs, "A" and "B", may be provided to a computation module 1502 associate with a memoization module 1504 operating in the manner discussed above. For example, the memoization module 1504 may, based on the received inputs, determine if an output for the associated inputs has been previously computed and is available in persistent storage. If the previously computed output is available, the memoization module 1504 may provide this output as an output for the computation. If the previously computed output is not available, the computation module 1502 may perform the computation. The output of the computation module 1502 may be provided to the memoization module 1504 for persistent storage and use in connection with future computations.

Figure 16:
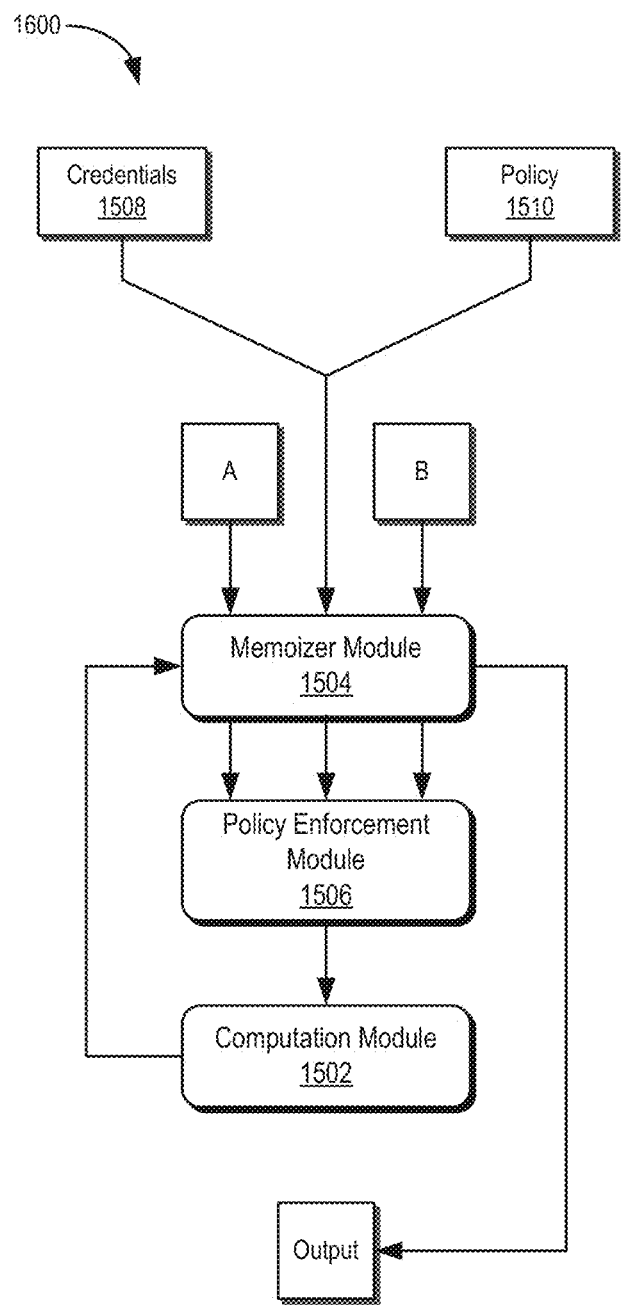
FIG. 16 illustrates a conceptual diagram of another computation implementing policy-driven memoization processes consistent with embodiments of the present disclosure.

FIG. 16 illustrates a conceptual diagram 1600 of another policy-driven memoization processes consistent with some embodiments of the present disclosure. As discussed above, in certain embodiments, credential information and/or policy information and/or hashes thereof may be persistently stored to increase look-up efficiency in connection with future computations, in addition to computation inputs, outputs, and/or hashes thereof. Accordingly, in the illustrated example process, the credentials 1508 and policy information 1510 may be provided to a memoization module 1504 in addition to the computation inputs, and/or outputs. Accordingly, in future computations, when the same inputs, credentials 1508, and/or policy information 1510 are provided, an associated persistently stored output may be accessed by the memoization module 1504 and provided as a computational output.

Figure 17:
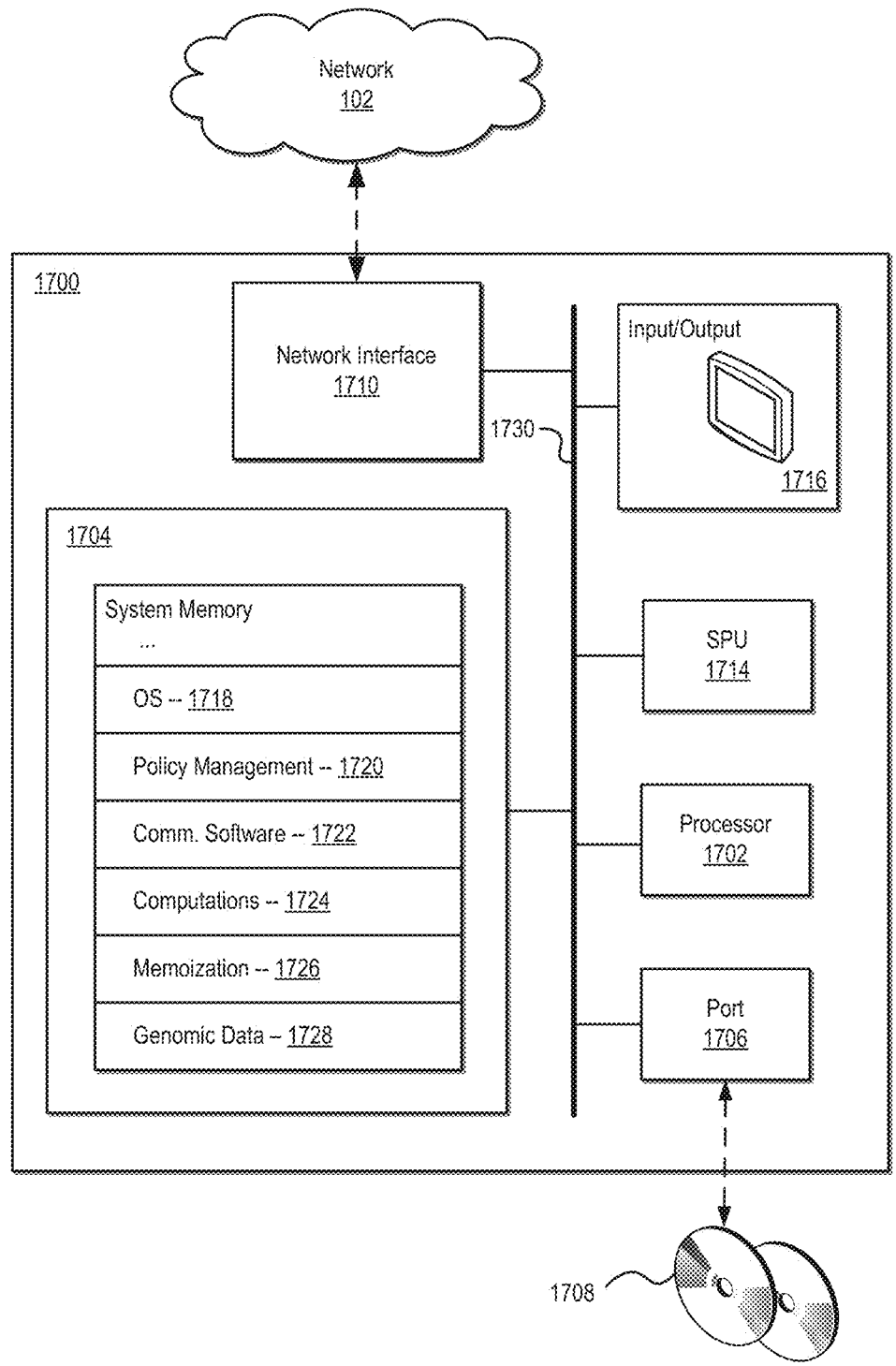
FIG. 17 illustrates an exemplary system that may be used to implement embodiments of the systems and methods of the present disclosure.

FIG. 17 illustrates an exemplary system 1700 that may be used to implement embodiments of the systems and methods disclosed herein. The exemplary system 1700 may comprise a computer system or other device that may perform the operations disclosed herein. For example, system 1700 might comprise a personal computer, a server system, a mobile device (e.g., a smartphone, a tablet, etc.), and/or the like. As illustrated in FIG. 17, the system 1700 may include, for example: a processing unit 1702; system memory 1704, which may include some combination of high speed random access memory ("RAM"), non-volatile memory ("ROM"), and/or one or more bulk non-volatile computer-readable storage mediums (e.g., a hard disk, flash memory, etc.) for storing programs and other data for use and execution by the processing unit 1702; a port 1706 for interfacing with removable memory 1708 that may include one or more diskettes, optical storage mediums (e.g., flash memory, thumb drives, USB dongles, compact discs, DVDs, etc.) and/or other computer-readable storage mediums; a network interface 1710 for communicating with other systems via one or more networks 102 using one or more communication technologies; a user interface 1716 that may include a display and/or one or more input/output devices such as, for example, a touchscreen, a keyboard, a mouse, a track pad, and/or the like; and one or more busses 1730 for communicatively coupling the elements of the system 1700.

In some embodiments, the system 1700 may, alternatively or in addition, include an SPU 1714 that is protected from tampering by a user of system 1700 or other entities by utilizing physical and/or virtual security techniques. An SPU 1714 can help enhance the security of sensitive operations such as trusted credential and/or key management, secure genomic data management, and other aspects of the systems and methods disclosed herein. In certain embodiments, the SPU 1714 may operate in a logically secure processing domain and be configured to protect and operate on secret information. In some embodiments, the SPU 1714 may include internal memory storing executable instructions or programs configured to enable to the SPU 1714 to perform secure operations. For example, in some embodiments an SPU 1714 such as described in commonly-assigned U.S. Pat. No. 7,430,585 ("the '585 patent") and/or U.S. Pat. No. 5,892,900 ("the '900 patent") could be used.

The operation of the system 1700 may be generally controlled by a processing unit 1702 and/or a SPU 1714 operating by executing software instructions and programs stored in the system memory 1704 (and/or other non-transitory computer-readable media, such as removable memory 1708). The system memory 1704 may store a variety of programs or modules for controlling the operation of the system 1700. For example, the system memory 1704 may include an operating system ("OS") 1718 that may manage and coordinate, at least in part, system hardware resources and provide for common services for execution of various applications, and a policy management module 1720 configured to manage and/or enforce policy associated with genomic and/or other bioinformatic data. The system memory 1704 may further include, without limitation, communication software 1722 configured to enable in part communication within and by the system 1700, computations 1724 (e.g., computations configured to operate on genomic data or the like), a memoization module 1726 configured to implement memoization processes in connection with computations 1724 consistent with embodiments disclosed herein, and/or locally stored genomic data 1728.

The systems and methods disclosed herein are not inherently related to any particular computer, electronic control unit, or other apparatus and may be implemented by a suitable combination of hardware, software, and/or firmware. Software implementations may include one or more computer programs comprising code/instructions that, when executed by a processor, may cause the system to perform a method defined at least in part by the program instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions, that when executed by a processor, are configured to cause a computer system to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a magnetic disk, flash memory, integrated circuits, or any other non-transitory memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method for performing trusted computations on genomic data performed by a system comprising a processor and a non-transitory computer-readable storage medium storing instructions that, when executed by the processor, cause the system to perform the method, the method comprising:

receiving a first request, comprising a first set of one or more pieces of identification information, from a user system to perform a computation by a computational module, whereby the computation comprises analyzing a genomic data set to determine whether the genomic data set exhibits a particular variant indicative of a carrier status;

determining, based on the first set of one or more pieces of identification information, that a result of a prior computation using the first set of one or more pieces of identification information is not stored in a persistent storage, wherein the determination comprises: (i) computing a hash of the first set of one or more pieces of identification information, (ii) determining that the hash of the first set of one or more pieces of identification information is not stored in the persistent storage, and (iii) based on the determination, determining that the result of the prior computation is not stored in the persistent storage;
storing information associated with the first set of one or more pieces of identification information in the persistent storage;
generating, based on the first set of one or more pieces of identification information, a result of the computation using the genomic data set;
storing the result of the computation in the persistent storage; and
sending the result of the computation to the user system.

2. The method of claim 1, wherein the method further comprises:
receiving a second request to perform the computation by the computational module using the genomic data set, the second request comprising the first set of one or more pieces of identification information;
determining, based on the first set of one or more pieces of identification information, that the result of the computation is stored in the persistent storage;
accessing the result of the computation from the persistent storage; and
sending the result of the computation to a system associated with the second request.

3. The method of claim 1, wherein the first set of one or more pieces of identification information comprises authentication information.

4. The method of claim 1, wherein the first set of one or more pieces of identification information comprises policy information associated with the genomic data set.

5. The method of claim 1, wherein the first set of one or more pieces of identification information comprises a cohort selection associated with the genomic data set.

6. The method of claim 1, wherein the first set of one or more pieces of identification information comprises instruction information associated with the computation.

7. The method of claim 1, wherein the method further comprises associating the information associated with the first set of one or more pieces of identification information with the result of the computation in the persistent storage.

8. The method of claim 1, wherein the information associated with the first set of one or more pieces of identification information comprises the computed hash of the first set of one or more pieces of identification information.

9. The method of claim 1, wherein the information associated with the first set of one or more pieces of identification information comprises the first set of one or more pieces of identification information.

10. The method of claim 1, wherein the genomic data set comprises human genomic data.

11. The method of claim 1, wherein the system comprises a distributed computing system, and wherein the computational module is associated with a first computing domain of the distributed computing system and the persistent storage is associated with a second computing domain of the distributed computing system.

12. A method for performing trusted computations on genomic data performed by a distributed computing system comprising a processor, and a non-transitory computer-readable storage medium storing instructions that, when executed by the processor, cause the system to perform the method, the method comprising:
receiving a first request, comprising a first set of one or more pieces of identification information, from a user system to perform a computation by a computational module associated with a first computing domain of the distributed computing system, whereby the computation comprises analyzing a genomic data set to determine whether the genomic data set exhibits a particular variant indicative of a carrier status;
determining, based on the first set of one or more pieces of identification information, that a result of a prior computation using the first set of one or more pieces of identification information is not stored in a persistent storage associated with a second computing domain of the distributed computing system;
storing information associated with the first set of one or more pieces of identification information in the persistent storage;
generating, based on the first set of one or more pieces of identification information, a result of the computation using the genomic data set;
storing the result of the computation in the persistent storage; and
sending the result of the computation to the user system.

13. The method of claim 12, wherein determining that the result of a prior computation is not stored in the persistent storage comprises:
computing a hash of the first set of one more pieces of identification information;
determining that the hash of the first set of one or more pieces of identification information is not stored in the persistent storage; and
based on the determination, determining that the result of the prior computation is not stored in the persistent storage.

14. The method of claim 12, wherein the method further comprises:
receiving a second request to perform the computation by the computational module using the genomic data set, the second request comprising the first set of one or more pieces of identification information;
determining, based on the first set of one or more pieces of identification information, that the result of the computation is stored in the persistent storage;
accessing the result of the computation from the persistent storage; and
sending the result of the computation to a system associated with the second request.

15. The method of claim 12, wherein the first set of one or more pieces of identification information comprises authentication information.

16. The method of claim 12, wherein the first set of one or more pieces of identification information comprises policy information associated with the genomic data set.

17. The method of claim 12, wherein the first set of one or more pieces of identification information comprises a cohort selection associated with the genomic data set.

18. The method of claim 12, wherein the first set of one or more pieces of identification information comprises instruction information associated with the computation.

19. The method of claim 12, wherein the method further comprises associating the information associated with the first set of one or more pieces of identification information with the result of the computation in the persistent storage.

20. The method of claim 12, wherein the information associated with the first set of one or more pieces of identification information comprises a computed hash of the first set of one or more pieces of identification information.

21. The method of claim 12, wherein the information associated with the first set of one or more pieces of identification information comprises the first set of one or more pieces of identification information.

22. The method of claim 12, wherein the genomic data set comprises human genomic data.

* * * * *

UNITED STATES PATENT AND TRADEMARK OFFICE
CERTIFICATE OF CORRECTION

PATENT NO. : 9,306,981 B2
APPLICATION NO. : 14/260714
DATED : April 5, 2016
INVENTOR(S) : Jarl Nilsson and William Knox Carey It is certified that error appears in the above-identified patent and that said Letters Patent is hereby corrected as shown below:

Claims

At Column 24, line 23, claim 13, reads "set of one more pieces" should read --set of one or more pieces--.

Signed and Sealed this
Nineteenth Day of July, 2016

Michelle K. Lee
*Director of the United States Patent and Trademark Office*